(12) United States Patent
Yacoub

(10) Patent No.: US 9,784,721 B2
(45) Date of Patent: Oct. 10, 2017

(54) DETERMINATION OF A DEGREE OF AGING OF AN OXIDIZING CATALYTIC CONVERTER

(71) Applicant: Ford Global Technologies, LLC, Dearborn, MI (US)

(72) Inventor: Yasser Mohamed sayed Yacoub, Cologne (DE)

(73) Assignee: Ford Global Technologies, LLC, Dearborn, MI (US)

( * ) Notice: Subject to any disclaimer, the term of this patent is extended or adjusted under 35 U.S.C. 154(b) by 77 days.

(21) Appl. No.: 14/169,936

(22) Filed: Jan. 31, 2014

(65) Prior Publication Data
US 2014/0220691 A1    Aug. 7, 2014

(30) Foreign Application Priority Data
Feb. 1, 2013    (DE) .................. 10 2013 201 695

(51) Int. Cl.
*G01N 33/00* (2006.01)
*F01N 11/00* (2006.01)
*F01N 3/10* (2006.01)

(52) U.S. Cl.
CPC ......... *G01N 33/0004* (2013.01); *F01N 3/103* (2013.01); *F01N 11/00* (2013.01); *F01N 2550/20* (2013.01); *F01N 2900/1602* (2013.01); *Y02T 10/47* (2013.01)

(58) Field of Classification Search
CPC ..... G01N 33/0004; F01N 11/00; F01N 3/103; F01N 2550/20; F01N 2900/1602; Y02T 10/47

USPC ............................................... 422/98; 436/37
See application file for complete search history.

(56) References Cited

U.S. PATENT DOCUMENTS

| 4,134,860 | A | * | 1/1979 | Hindin | ................. B01J 37/0215 |
| | | | | | 502/325 |
| 4,414,940 | A | * | 11/1983 | Loyd | ........................ F02B 3/00 |
| | | | | | 123/275 |
| 4,510,261 | A | * | 4/1985 | Pereira | ................. B01D 53/945 |
| | | | | | 423/213.5 |

(Continued)

FOREIGN PATENT DOCUMENTS

| DE | 4039429 A1 | 6/1992 |
| DE | 4227207 A1 | 2/1994 |

(Continued)

OTHER PUBLICATIONS

Agarwal, D. et al, Applied Energy 2011, 88, 2900-2907.*

(Continued)

*Primary Examiner* — Arlen Soderquist
(74) *Attorney, Agent, or Firm* — Julia Voutyras; McCoy Russell LLP

(57) ABSTRACT

A method for determining a degree of aging of an oxidizing catalytic converter in an exhaust system of an internal combustion engine is provided. The method comprises generating a temporary increase in carbon monoxide levels in an exhaust gas stream, monitoring subsequent oxidizing action and determining a degree of aging of the oxidizing catalytic converter as a function of the measured oxidizing action. The method further comprises measuring a temperature rise during oxidation and correlating the aging of the converter to the speed of temperature rise.

19 Claims, 10 Drawing Sheets

(56) References Cited

U.S. PATENT DOCUMENTS

| | | | | |
|---|---|---|---|---|
| 4,757,045 A * | 7/1988 | Turner | B01D 53/945 | 423/213.5 |
| 4,771,029 A * | 9/1988 | Pereira | B01D 53/945 | 423/213.5 |
| 4,868,148 A * | 9/1989 | Henk | B01D 53/945 | 423/213.5 |
| 4,915,080 A * | 4/1990 | Nakaniwa | F02D 41/1475 | 123/691 |
| 5,041,407 A * | 8/1991 | Williamson | B01D 53/945 | 423/213.5 |
| 5,048,490 A * | 9/1991 | Nakaniwa | F02D 41/1495 | 123/479 |
| 5,088,281 A * | 2/1992 | Izutani | F01N 11/007 | 60/274 |
| 5,092,123 A * | 3/1992 | Nada | F02D 41/1441 | 123/691 |
| 5,119,628 A * | 6/1992 | Uema | F01N 11/007 | 60/274 |
| 5,175,997 A | 1/1993 | Blanke, Sr. | | |
| 5,282,383 A * | 2/1994 | Kayanuma | F01N 11/007 | 73/114.72 |
| 5,339,627 A * | 8/1994 | Baier | F01N 11/00 | 123/691 |
| 5,412,945 A * | 5/1995 | Katoh | B01D 53/02 | 423/213.7 |
| 5,431,012 A * | 7/1995 | Narula | F01N 11/00 | 60/276 |
| 5,487,270 A * | 1/1996 | Yamashita | F01N 11/007 | 60/276 |
| 5,622,047 A * | 4/1997 | Yamashita | F01N 11/007 | 60/274 |
| 5,822,982 A * | 10/1998 | Mitsutani | F01N 11/007 | 60/276 |
| 5,916,294 A * | 6/1999 | Naber | F01N 11/00 | 60/276 |
| 6,003,307 A * | 12/1999 | Naber | F01N 11/00 | 60/274 |
| 6,195,988 B1 * | 3/2001 | Yasui | F02D 41/1403 | 123/674 |
| 6,502,386 B1 * | 1/2003 | Mazur | F01N 9/005 | 60/274 |
| 6,533,911 B1 * | 3/2003 | Fujita | G01N 27/4075 | 204/424 |
| 6,651,422 B1 * | 11/2003 | LeGare | F01N 11/002 | 60/274 |
| 7,188,470 B2 * | 3/2007 | Bosteels | B01D 53/9431 | 123/670 |
| 7,276,212 B2 * | 10/2007 | Hu | B01D 53/9454 | 422/168 |
| 7,416,572 B2 * | 8/2008 | Wakao | F02M 25/12 | 436/34 |
| 7,694,506 B2 * | 4/2010 | Berger | F01N 11/007 | 60/274 |
| 7,779,620 B2 * | 8/2010 | Ishikawa | F01N 11/007 | 60/277 |
| 7,886,523 B1 * | 2/2011 | Legare | F02D 41/008 | 60/274 |
| 2003/0061860 A1 * | 4/2003 | Hu | B01D 53/9454 | 73/23.31 |
| 2004/0205998 A1 * | 10/2004 | Wakao | F02M 25/12 | 48/198.7 |
| 2007/0220961 A1 * | 9/2007 | Berger | F01N 11/007 | 73/114.75 |
| 2007/0227518 A1 * | 10/2007 | West | F01N 3/0842 | 123/673 |
| 2007/0234708 A1 * | 10/2007 | Jones | F01N 11/00 | 60/277 |
| 2009/0158715 A1 * | 6/2009 | Stroh | F01N 3/0814 | 60/295 |
| 2011/0056280 A1 * | 3/2011 | Votsmeier | F01N 11/002 | 73/114.75 |
| 2012/0047874 A1 * | 3/2012 | Schmieg | B01D 53/9418 | 60/274 |
| 2013/0019589 A1 * | 1/2013 | Kim | B01D 53/9477 | 60/297 |
| 2015/0000253 A1 * | 1/2015 | Kim | F01N 3/0814 | 60/274 |

FOREIGN PATENT DOCUMENTS

| | | | |
|---|---|---|---|
| DE | 102011102008 A1 | | 11/2012 |
| EP | 1052385 A2 | | 11/2000 |
| JP | 2002-332904 | * | 11/2002 |
| JP | 2006-118358 | * | 5/2006 |
| JP | 2010-223180 | * | 10/2010 |
| JP | 2011-1833 | * | 1/2011 |
| JP | 2011-21938 | * | 2/2011 |

OTHER PUBLICATIONS

Sayin, C. et al, Fuel 2010, 89, 1407-1414.*
Tsolakis, A. et al, Energy Fuels 2010, 24, 302-308.*
Senthil, R. et al, Engineering, 2011, 3, 1132-1136.*
Hussain, J. et al, International Journal of Energy Engineering 2012, 2, 285-292.*
Murthy, K. et al, International Journal of Engineering Research and Development 2012, 1, 36-42.*

* cited by examiner

DETERMINATION OF A DEGREE OF AGING OF AN OXIDIZING CATALYTIC CONVERTER

CROSS REFERENCE TO RELATED APPLICATIONS

The present application claims priority to German Patent Application No. 102013201695.6, filed on Feb. 1, 2013, the entire contents of which are incorporated herein by reference for all purposes.

TECHNICAL FIELD

The invention relates to a method for determining a degree of aging of an oxidizing catalytic converter arranged in an exhaust of an internal combustion engine.

BACKGROUND AND SUMMARY

Oxidizing catalytic converters may be present in the exhaust stream of motor vehicles in order to reduce the emission of pollutants produced during combustion. For example, unburnt fuel and carbon monoxide (CO) may be converted to less toxic substances, such as carbon dioxide and water, before being released to the atmosphere.

However, high exhaust temperatures and the heat released during oxidation can cause aging and degradation of an oxidizing catalytic converter resulting in increased emissions. Various methods may be employed to monitor the aging and consequent degradation in performance of an oxidizing catalytic converter. In one method, the concentration of unburnt hydrocarbons in the exhaust may be increased via post-injection or direct injection of fuel into the exhaust and a temperature rise within the oxidizing catalytic converter may be observed.

The inventors herein have identified potential issues with the above approach. The temperature increase within the oxidizing catalytic converter caused by oxidizing a higher concentration of unburnt hydrocarbons is minimal: about 10 to 20° C. Therefore, the reliability with which a distinction can be made between a robust (less aged) and a degraded (greatly aged) oxidizing catalytic converter is lower. Further, the oxidizing catalytic converter may store hydrocarbons which may be oxidized only after the catalytic converter has reached light-off temperatures thus, inadvertently contributing to the increase in catalyst temperature and resulting in erroneous readings.

The inventors herein have recognized the above issues and identified an approach to at least partly address the issues. In one example approach, a method for monitoring the aging of an oxidizing catalytic converter in the exhaust stream of an engine is provided. The method comprises monitoring oxidation action of the converter after artificially generating an increase in feedgas carbon monoxide levels. A degree of aging of the catalytic converter is determined based on the oxidizing action of the converter.

In one example, when the oxidizing catalytic converter is above its light-off temperature, carbon monoxide levels in the exhaust stream may be artificially increased for short durations, for e.g., by operating the engine under a lean mode, and oxidation action may be monitored. Herein, oxidation action may be measured based on the oxidation efficiency of carbon monoxide. An aged oxidizing catalytic converter may be indicated when carbon monoxide oxidation efficiency is reduced and a fraction of carbon monoxide in the gases exiting the oxidizing catalytic converter are higher than an allowable threshold.

In another example, oxidation action may be evaluated during temporarily increased carbon monoxide conditions by monitoring the temperature rise within the oxidizing catalytic converter during the oxidation process. An aged oxidizing catalytic converter may be indicated when the rate of temperature increase within the oxidizing catalytic converter is slower than an expected rate.

In this way, aging can be assessed by artificially increasing feedgas carbon monoxide levels to enable more reliable data regarding oxidizing action of the catalytic converter. By focusing on the oxidation of carbon monoxide, instead of unburnt hydrocarbons, more accurate results may be obtained because the oxidation of carbon monoxide causes a significant temperature increase in the oxidizing catalytic converter. Additionally, carbon monoxide, unlike unburnt hydrocarbons, is not stored within the oxidizing catalytic converter prior to light-off temperature. Thus, an observed temperature rise within the oxidizing catalytic converter may be correlated with the oxidation of carbon monoxide flowing through the catalyst. By increasing carbon monoxide levels after light-off, emissions can be kept within acceptable limits. By operating the engine in a lean mode, the content of unburnt hydrocarbons in the exhaust gas stream can be held at lower concentrations while providing sufficient carbon monoxide for catalytic converter diagnosis.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
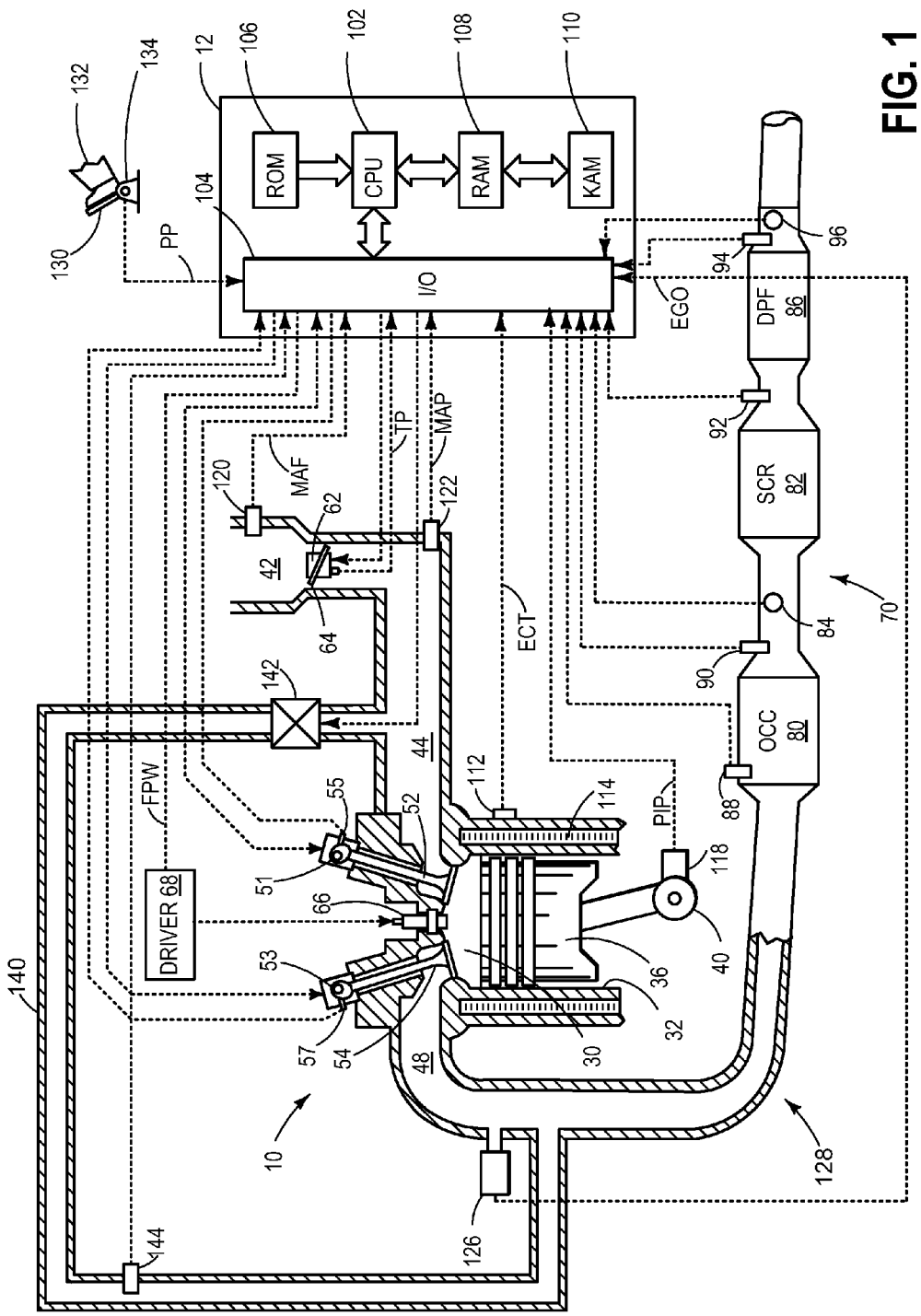
FIG. 1 portrays a schematic diagram of an engine with an oxidizing catalytic converter (OCC) system.
Figure 6:
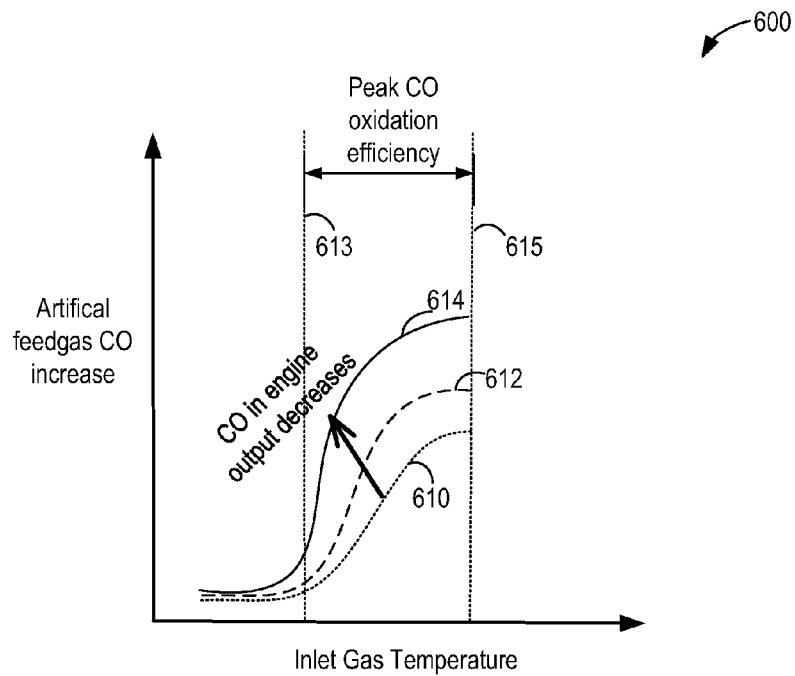
FIG. 6 shows a graph depicting the artificial increase necessary in feedgas CO levels based on initial CO levels in exhaust gases exiting the engine.
Figure 7:
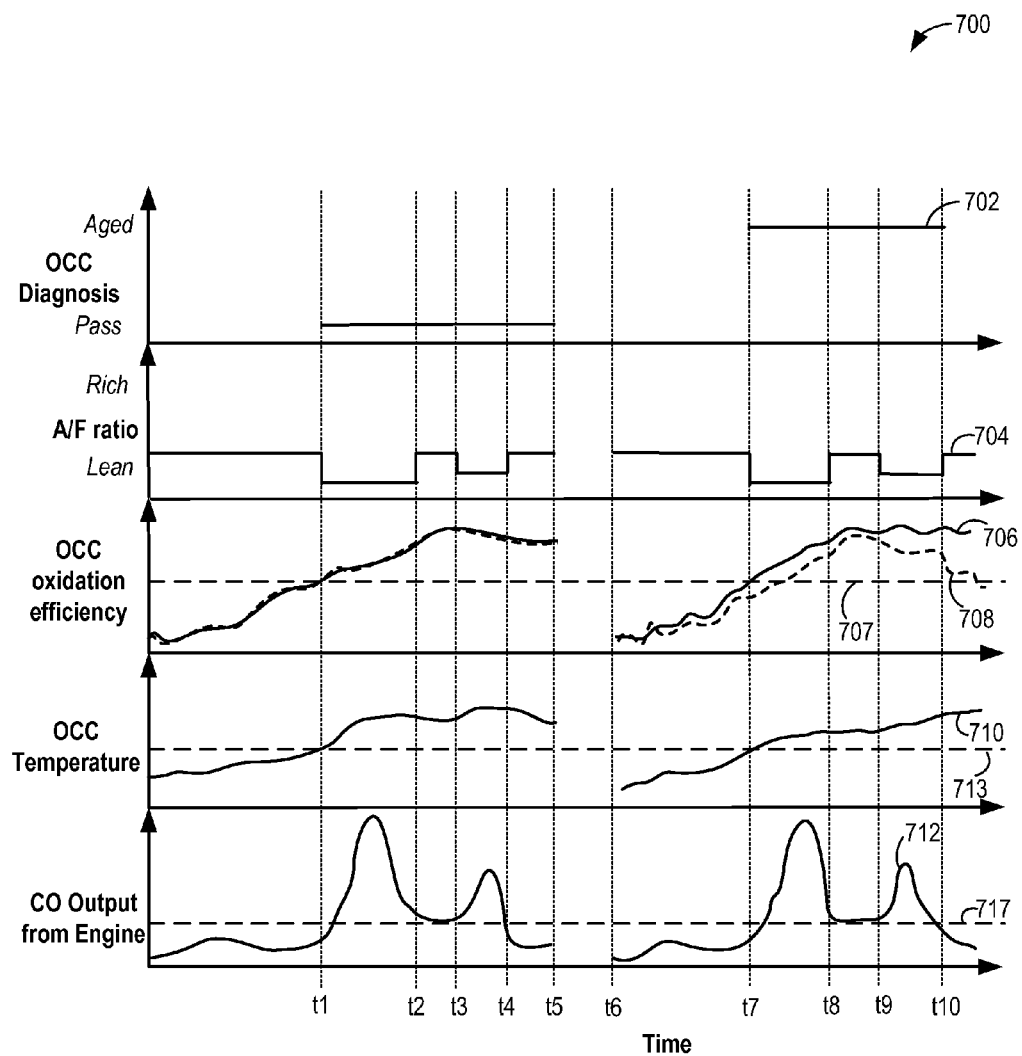
FIG. 7 is an example diagnostic operation of an OCC based on oxidation efficiency of the OCC, according to the present disclosure.
Figure 8:
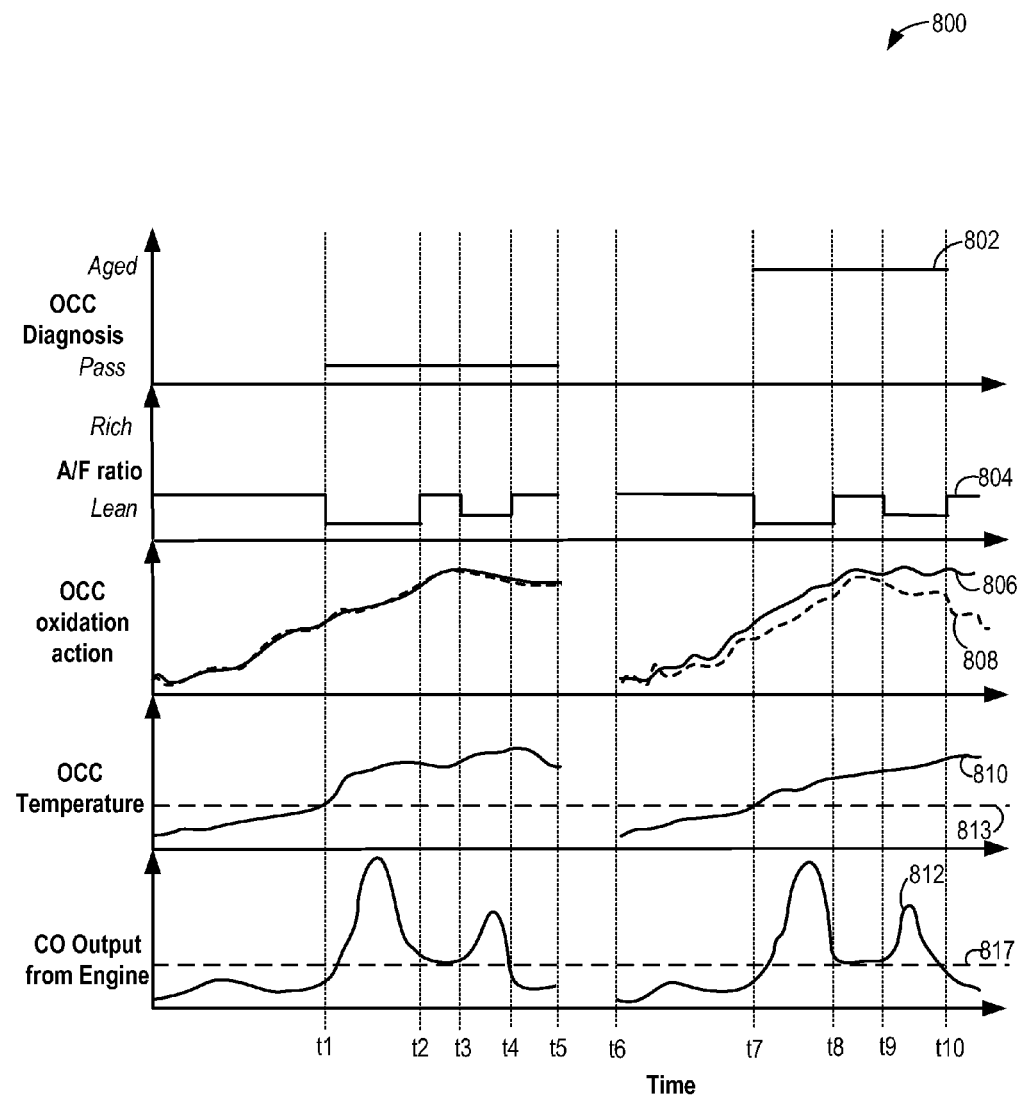
FIG. 8 is an example diagnostic operation of an OCC based on temperature rise within the OCC, according to the present disclosure.

The following description relates to methods and systems for detecting a degree of aging of an oxidizing catalytic converter (OCC) placed in the exhaust system of an engine, such as that shown in FIG. 1. A controller of the engine may be configured to perform a routine, such as the example routine of FIG. 2, to diagnose the aging of an OCC under artificially enhanced carbon monoxide (CO) conditions. When the OCC is operating at a temperature above light-off and within its peak oxidation range (FIG. 5), CO levels in exhaust gases exiting the engine may be artificially increased and the necessary increase may depend on the original levels of CO in the exhaust gases (FIG. 6). Two different types of aging diagnosis may be used where one type is based on the oxidation efficiency of the OCC (FIG. 3) and another is based on the temperature rise within the OCC during an oxidation reaction (FIG. 4). Artificially augmenting feedgas CO levels to the OCC for short durations (FIG. 9) while maintaining low unburnt hydrocarbon levels (FIG. 10) can help improve the accuracy of sensor readings during selected conditions. Temperature rise within the OCC during oxidation (FIGS. 11 and 12) can be measured and compared to an expected temperature rise for a non-aged OCC (FIG. 13) to diagnose aging (FIG. 8). Oxidation efficiency measured during the artificial increase in CO levels can provide an alternative or a more expensive mode for determining OCC aging (FIG. 7).

Referring now to FIG. 1, it shows a schematic diagram with one cylinder of multi-cylinder engine 10, which may be included in a propulsion system of a vehicle. Engine 10 may be controlled at least partially by a control system including a controller 12 and by input from a vehicle operator 132 via an input device 130. In this example, input device 130 includes an accelerator pedal and a pedal position sensor 134 for generating a proportional pedal position signal PP. A combustion chamber (i.e., cylinder) 30 of the engine 10 may include combustion chamber walls 32 with a piston 36 positioned therein. Piston 36 may be coupled to a crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to the crankshaft 40 via a flywheel (not shown) to enable a starting operation of the engine 10.

Combustion chamber 30 may receive intake air from an intake manifold 44 via an intake passage 42 and may exhaust combustion gases via an exhaust passage 48. The intake manifold 44 and the exhaust passage 48 can selectively communicate with the combustion chamber 30 via intake valve 52 and exhaust valve 54 respectively. In some embodiments, the combustion chamber 30 may include two or more intake valves and/or two or more exhaust valves.

In the example depicted in FIG. 1, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 12 to vary valve operation. The position of the intake valve 52 and the exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. Fuel injector 66 is shown coupled directly to the cylinder 30 for injecting fuel directly therein. It will also be appreciated that the cylinder 30 may receive fuel from a plurality of injections during a combustion cycle.

In one example, engine 10 may be a diesel engine that combusts air and diesel fuel through compression ignition. In other non-limiting embodiments, engine 10 may combust a different fuel including gasoline, biodiesel, or an alcohol containing fuel blend (e.g., gasoline and ethanol or gasoline and methanol) through compression ignition and/or spark ignition.

The intake passage 42 may include a throttle 62 having a throttle plate 64. In this particular example, the position of the throttle plate 64 may be varied by the controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by throttle position signal TP. The intake passage 42 may include a mass air flow sensor 120 and a manifold air pressure sensor 122 for providing respective signals MAF and MAP to the controller 12.

Further, an exhaust gas recirculation (EGR) system may route a desired portion of exhaust gas from the exhaust passage 48 to the intake manifold 44 via an EGR passage 140. The amount of EGR provided may be varied by controller 12 via an EGR valve 142. As depicted, the EGR system further includes an EGR sensor 144 which may be arranged within the EGR passage 140 and may provide an indication of one or more of pressure, temperature, and concentration of the exhaust gas.

An exhaust system 128 includes an exhaust gas sensor 126 coupled to the exhaust passage 48 upstream of an exhaust gas treatment system 70. Exhaust gas sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), NOx, HC, or a CO sensor. The exhaust gas treatment system 70 is shown arranged along the exhaust passage 48 downstream of the exhaust gas sensor 126.

The exhaust gas treatment system 70 may include a plurality of emission control devices. For example, the exhaust gas treatment system 70 may include an oxidizing catalytic converter (OCC) 80 disposed along exhaust gas passage 48. A selective catalytic reduction (SCR) system 82 may be disposed along the exhaust gas conduit downstream of OCC 80. A urea sprayer 84 (or any suitable ammonia source) may be disposed upstream of SCR 82 and downstream of OCC 80. A diesel particulate filter (DPF) 86 may be disposed along the exhaust conduit downstream of SCR 82.

Temperature sensors 88, 90, 92, and 94 may be disposed at points along the exhaust gas conduit both upstream and downstream of each device in the exhaust treatment system 70. Temperature sensor 88, as shown in FIG. 1, may be placed in OCC 80 and may be used to detect and avoid overheating of OCC 80. It may also provide notification that the OCC has reached its light-off temperature.

An additional carbon monoxide sensor 96 may be disposed downstream of the exhaust treatment system 70 to evaluate the oxidizing action of the OCC by measuring a carbon monoxide (CO) leakage from the OCC. Herein, carbon monoxide leakage is the CO content in the gases exiting the OCC or the fraction of CO exiting the OCC without being oxidized into carbon dioxide. Oxidation efficiency of the OCC may be calculated by comparing the CO levels entering the catalytic converter with the CO levels exiting the OCC. The additional CO sensor 96, however, may increase overall costs of the system. Sensor 96 may also be a sensor which measures CO leakage indirectly by means of the oxygen partial pressure. In this case, CO levels in gases exiting the OCC are inferred from the oxygen remaining in the exhaust gas. In other embodiments, CO sensor 96 may be absent whereupon oxidation action of the OCC may be evaluated by monitoring a rate of temperature increase based on feedback from temperature sensor 88.

It should be understood that exhaust treatment system 70 may include a plurality of treatment device configurations not shown in FIG. 1. In one example, the exhaust treatment system may include solely an OCC. In another example, the exhaust treatment system may include an OCC followed downstream by a DPF. In another example, the exhaust treatment system may include an OCC followed downstream by a DPF and a SCR. In still another example, SCR 82 shown in FIG. 1 may be replaced with a lean NOx trap (LNT). Further, the order of the different catalysts and filters in the exhaust treatment system may also vary. The number of temperature sensors disposed within the exhaust treatment system may vary according to the application. Though the CO sensor 96 is shown in FIG. 1 at a point located downstream of DPF 60, it may be located upstream of any of the bricks in the treatment system 70 as long as it is in a position downstream of the OCC.

Controller 12 is shown in FIG. 1 as a microcomputer, including a microprocessor unit 102, input/output ports 104, an electronic storage medium for executable programs and calibration values shown as a read only memory chip 106 in this particular example, random access memory 108, keep alive memory 110, and a data bus. The controller 12 may be in communication with and, therefore, receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; temperature of the OCC from sensor 88, a profile ignition pickup signal (PIP) from a Hall effect sensor 118 (or other type) coupled to the crankshaft 40; throttle position (TP) from a throttle position sensor; absolute manifold pressure signal, MAP, from the pressure sensor 122; and exhaust constituent concentration from the exhaust gas sensors 126 and CO concentration from sensor 96. Engine speed signal, RPM, may be generated by controller 12 from signal PIP.

The storage medium read-only memory chip 106 can be programmed with non-transitory, computer readable data representing instructions executable by the microprocessor unit 102 for performing the routines described below as well as other variants that are anticipated but not specifically listed. Example routines are described herein with reference to FIGS. 2-4.

As described above, FIG. 1 shows only one cylinder of a multi-cylinder engine, and each cylinder may similarly include its own set of intake/exhaust valves, fuel injector, etc.

Figure 2:
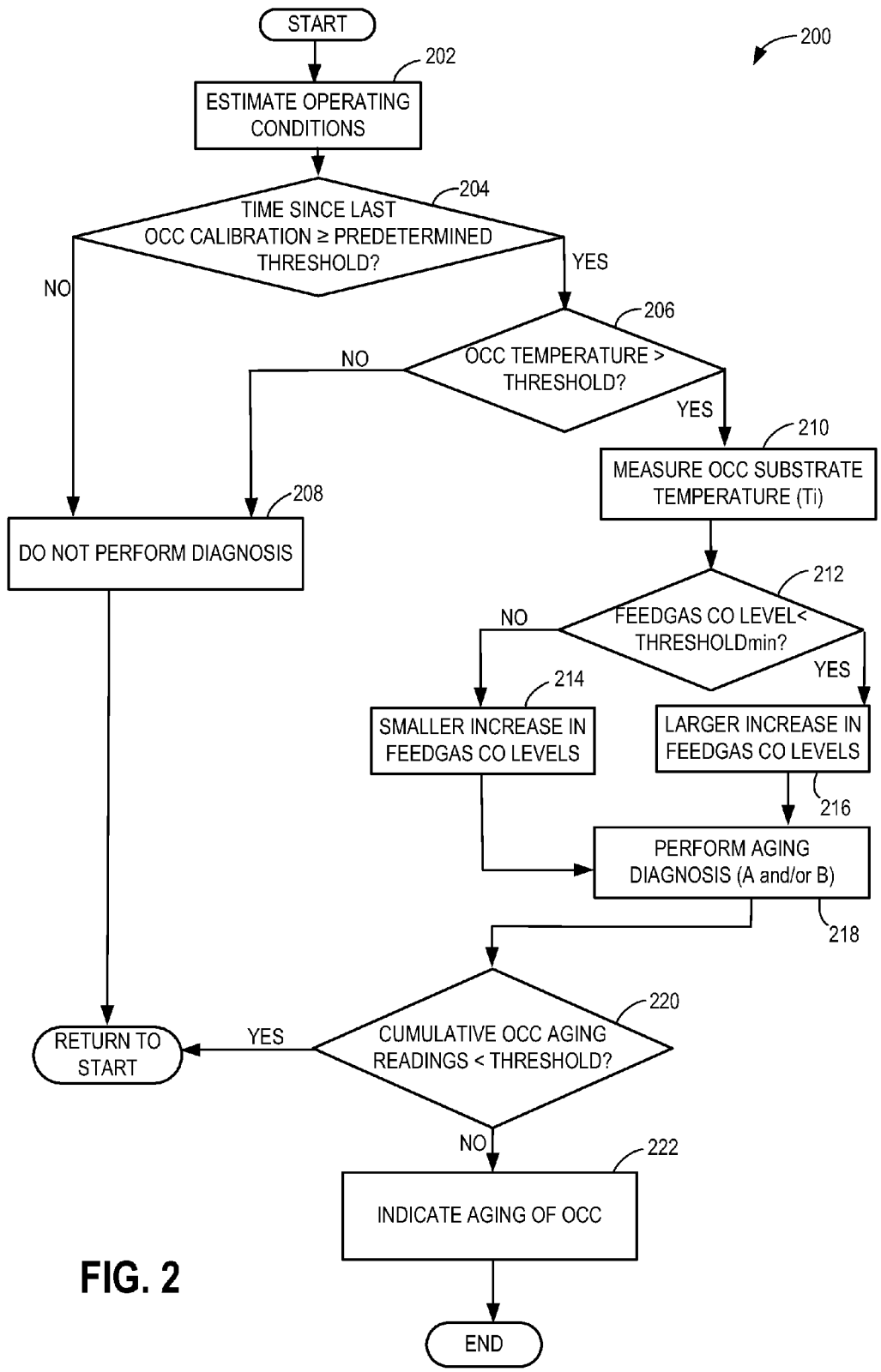
FIG. 2 depicts a flowchart illustrating a routine to diagnose a degree of ageing of an OCC.

Now turning to FIG. 2 where an example routine 200 is shown for conducting an aging diagnosis of an OCC. Specifically, the routine executes the diagnosis sequence when the substrate temperature of the OCC is above light-off and artificially raises CO levels during the diagnosis in the exhaust to allow for more reliable sensor feedback. Oxidizing action of the OCC may be evaluated either by type A or type B of diagnosis which will be described in more detail in reference to FIGS. 3 and 4. Aging of the OCC may be indicated when a threshold is surpassed. The indication of aging may include a message displayed to the vehicle operator that degradation has been identified, and may further include setting a diagnostic code stored in non-transitory memory corresponding to aging of the OCC, and specifically identifying the OCC as the component that is degraded. The diagnostic code may be retrievable through an interface port on-board the vehicle.

At 202, routine 200 includes determining engine operating conditions. Operating conditions may include engine speed and load, engine temperature, engine out CO levels, OCC oxidation efficiency (as determined based on feedback from the exhaust sensors, for example) and OCC light-off (e.g., whether or not the OCC has reached its light-off temperature). For example, the diagnostic may wait until OCC reaches light-off before proceeding. At 204, it may be confirmed if it is an appropriate time to perform an OCC diagnostic routine. The OCC diagnostic routine may be indicated if a threshold amount of time has elapsed since a previous routine was performed. If the OCC diagnostic routine is not indicated, routine 200 returns to start.

If the time elapsed since a previous diagnostic routine is more than a threshold, at 206 it may be determined if OCC temperature is above a minimum threshold. OCC temperature may be determined from temperature sensor 88 (FIG. 1) placed within the catalytic converter. For example, the minimum temperature threshold may be the light-off temperature. In another example, the minimum temperature may be that over which OCC oxidation efficiency is at a desired threshold level, greater than light-off efficiency and at or below peak efficiency. As another example, the routine may determine whether the temperature is such that the efficiency is within 10% of peak efficiency for a non-aged OCC.

Figure 5:
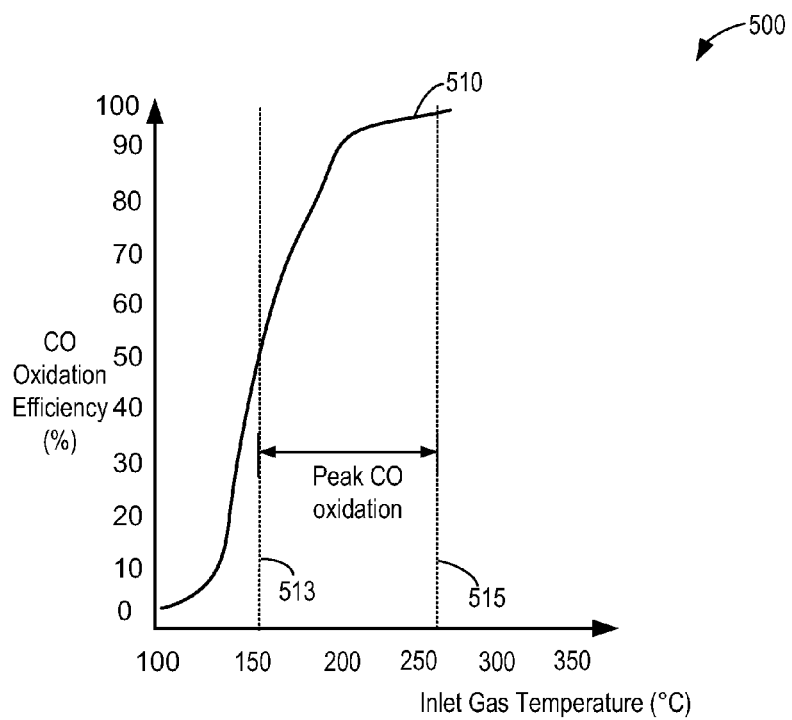
FIG. 5 shows a plot of CO oxidation efficiency versus OCC inlet gas temperature.

Referring now to FIG. 5, it shows a plot of CO oxidation efficiency versus inlet gas (or feedgas) temperature. Map 500 represents an example of CO oxidation efficiency for OCC 80 of FIG. 1. The Y axis represents CO oxidation efficiency in percentage. The X axis represents OCC inlet gas temperature in degrees C.

Herein, oxidation efficiency plot 510 shows that an OCC may have low CO oxidation efficiency at temperatures below 150° C. For example, within the light-off temperature window of 120-150° C., CO oxidation efficiency increases from about 10% to about 50%. CO oxidation efficiency increases rapidly beyond vertical marker 513 and reaches about 95% at about 250° C. as indicated by vertical marker 515. Thus, the region between vertical markers 513 and 515 may be a predetermined OCC operating region for a desired CO oxidation efficiency. Further, in this example, vertical marker 513 represents the achievement of light-off temperature and the temperature threshold at step 206 of routine 200. Thus, routine 200 may enable the aging diagnosis only when OCC substrate temperature is above 120° C. and preferably above 150° C. so that at least 50% of the carbon monoxide is oxidized into carbon dioxide.

Returning now to FIG. 2, if the OCC temperature is below the minimum threshold, the routine may disable the aging diagnosis at 208 and may return to start. If the OCC temperature is above the threshold, at 210, the OCC substrate temperature is measured and noted as Ti. At 212, it may be determined if the levels of CO in the feedgas entering the OCC are greater than a minimum threshold. This helps determine the amount of artificial increase in CO generation that may be scheduled to provide a higher accuracy in oxidation efficiency measurements. In one example, CO levels in the exhaust may be higher because of cool engine operating temperatures. In another example, CO levels in exhaust gases may be lower due to steady state operating conditions.

Map 600 of FIG. 6 illustrates a relationship between CO levels in exhaust gases exiting the engine and the necessary artificial increases to feedgas CO levels. The Y-axis represents artificial increases to CO levels while the X-axis represents the temperature of the OCC.

Plot 610 depicts the variation in the scheduled artificial increases to CO levels in feedgas with temperature when CO levels in engine output is higher. Plot 612 shows the variation in scheduled artificial increases to CO levels when engine output of CO is lower while plot 614 demonstrates the variation when engine output of CO is lowest. Vertical markers 613 and 615 depict the peak oxidation efficiency range of the OCC.

It may be noted from map 600 that as CO levels in exhaust gases exiting the engine reduce, a larger artificial increase in CO levels is scheduled to raise feedgas CO levels in gases entering the OCC. For example, if the CO levels entering the OCC are 1500 ppm (parts per million) and the controller determines to raise CO levels to 3000 ppm, an increase of 1500 ppm is selected. If the CO levels in exhaust gases exiting the engine are about 500 ppm, the controller will increase feedgas CO levels by 2500 ppm to reach the scheduled 3000 ppm CO levels required for diagnosis.

The exhaust gas stream containing increased levels of CO may be adjusted to contain more carbon monoxide than C1 hydrocarbons, specifically at least three times or five times as much carbon monoxide as C1 hydrocarbons. C1 hydrocarbons are hydrocarbons which contain one carbon atom per molecule. However, even hydrocarbons containing more than one carbon atom can be converted into an equivalent value for C1 hydrocarbons in that their content can be multiplied by the number of carbon atoms contained in these hydrocarbons and is added to the overall content of C1 hydrocarbons. Thus, a content of 1000 ppm of octane in the exhaust gas stream corresponds to a content of 8000 ppm of C1 hydrocarbons. By maintaining a larger proportion of CO in the exhaust gas stream, hydrocarbons contained in the exhaust gas stream and likewise oxidized by the OCC are kept as low as possible. However, a residual content of hydrocarbons in the exhaust gas stream cannot be avoided entirely.

Thus, in one example, the carbon monoxide-containing exhaust gas stream may include at least 2500 ppm of CO while in another example, the CO levels may be more than 5000 ppm and in yet another example, the feedgas may contain more than 10,000 ppm of carbon monoxide. However, the concentration of C1 hydrocarbons in the exhaust stream may be maintained at less than 1500 ppm. By using elevated concentrations of CO in the feedgas, a higher accuracy in determining the degree of aging of the OCC can be achieved.

The artificial increase in CO levels may be performed for short durations to reduce a negative effect on emissions particularly if the OCC is aged. In one example, the temporary increase in CO levels may be induced for 10 seconds while in another example the duration may be as short as 5 seconds.

In one example, feedgas CO levels can be raised artificially by manipulating air fuel ratios in the intake flow particularly during cold start conditions. For example, the engine can be operated in a lean mode in order to generate a carbon monoxide-containing exhaust gas stream. The content of hydrocarbons in the exhaust gas stream may thereby be kept low and at the same time sufficient carbon monoxide may be generated. In yet another example, exhaust gas recirculation (EGR) may be increased to induce a higher concentration of CO in the exhaust.

Returning to step 212 of routine 200, if the CO levels in the gases exiting the cylinders are determined to be below a minimum threshold, a larger artificial increase in CO levels may be induced at step 216. If the CO levels are above a minimum threshold, a smaller artificial increase in CO levels may be generated at step 214. Two types of aging diagnosis may be performed by evaluating oxidation action of the OCC. The oxidizing action can be assessed in various ways including by measuring an oxidation efficiency and/or by measuring a change in OCC temperature during oxidation. The aim of the measurement is to establish the quantity of carbon monoxide oxidized by the OCC. The degree of aging of the OCC can be estimated from this measurement since an aged OCC may oxidize a relatively lower fraction of CO than a robust, fresh oxidizing catalytic converter.

Thus, at step 218, it may be determined if type A or type B of diagnosis is to be performed. Type A diagnoses aging based on oxidation efficiency while type B determines aging by measuring a rate of temperature increase during oxidation. The selection of type A or type B may be based on the presence of an additional CO sensor in the exhaust treatment system. For example, in the embodiment shown in FIG. 1, type A diagnosis may be chosen and CO sensor 96 may be used to measure CO leakage in the exhaust to calculate an oxidation efficiency. Herein, type B diagnosis may be performed in addition to type A diagnosis to obtain additional data on degradation of the OCC. The routine may thus use cumulative readings from both types of diagnoses to identify aging of the OCC. If the embodiment does not comprise an additional sensor 96, aging diagnosis may be performed using type B.

Each type of OCC aging diagnosis may evaluate oxidation action to relate it to the presence or absence of aging in the OCC. For example, a counter of aging readings may be incremented by one if calculated OCC oxidation efficiency is lower than an expected efficiency. Likewise, if calculated efficiency is comparable or higher than expected oxidation efficiency, the counter is not incremented. Thus, at 220, it may be determined if the cumulative OCC aging readings are higher than a minimum threshold. If it is established that the cumulative aging readings are higher than the threshold, routine 200 indicates a higher degree of aging of the OCC at 222 and may turn on a malfunction indicator lamp (MIL) on the dashboard. If the number of aging readings is determined to be lower than a threshold, routine 200 returns to the start and continues to perform diagnostic routines when operating conditions are met.

In this way, a controller may perform a routine to diagnose a degree of aging of an OCC. The diagnosis routine may be disabled if the OCC substrate temperature is below light-off. By increasing levels of CO in the exhaust gas stream exclusively when the OCC substrate temperature lies above a light-off temperature, maximum oxidation of the carbon monoxide may be ensured and tailpipe emissions of CO are maintained within acceptable limits. At lower temperatures, the OCC could be incorrectly diagnosed as being aged because oxidizing action is diminished below the light-off temperature.

Figure 3:
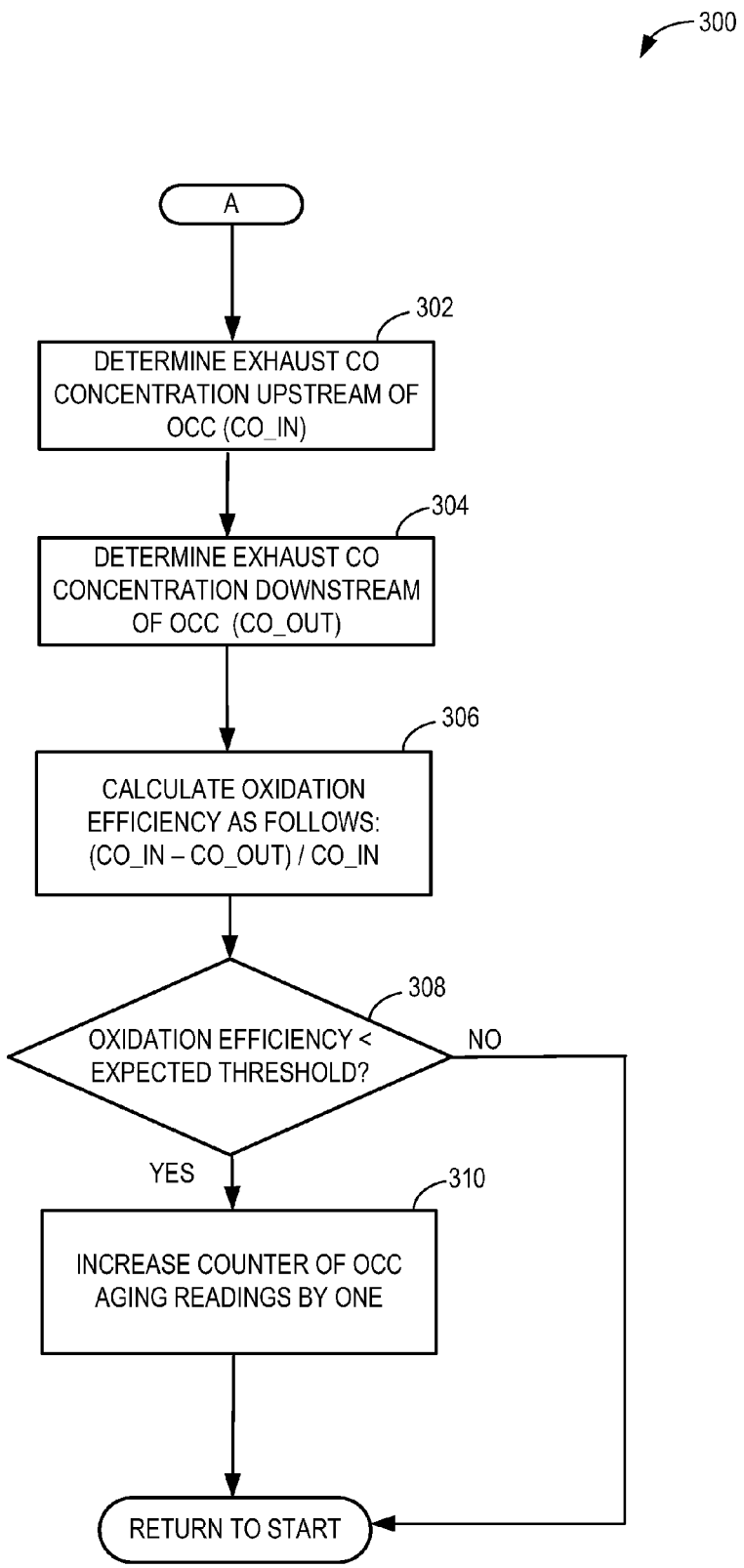
FIG. 3 shows a flowchart illustrating a routine for analyzing oxidation action of an OCC based on carbon monoxide (CO) oxidation efficiency.
Figure 4:
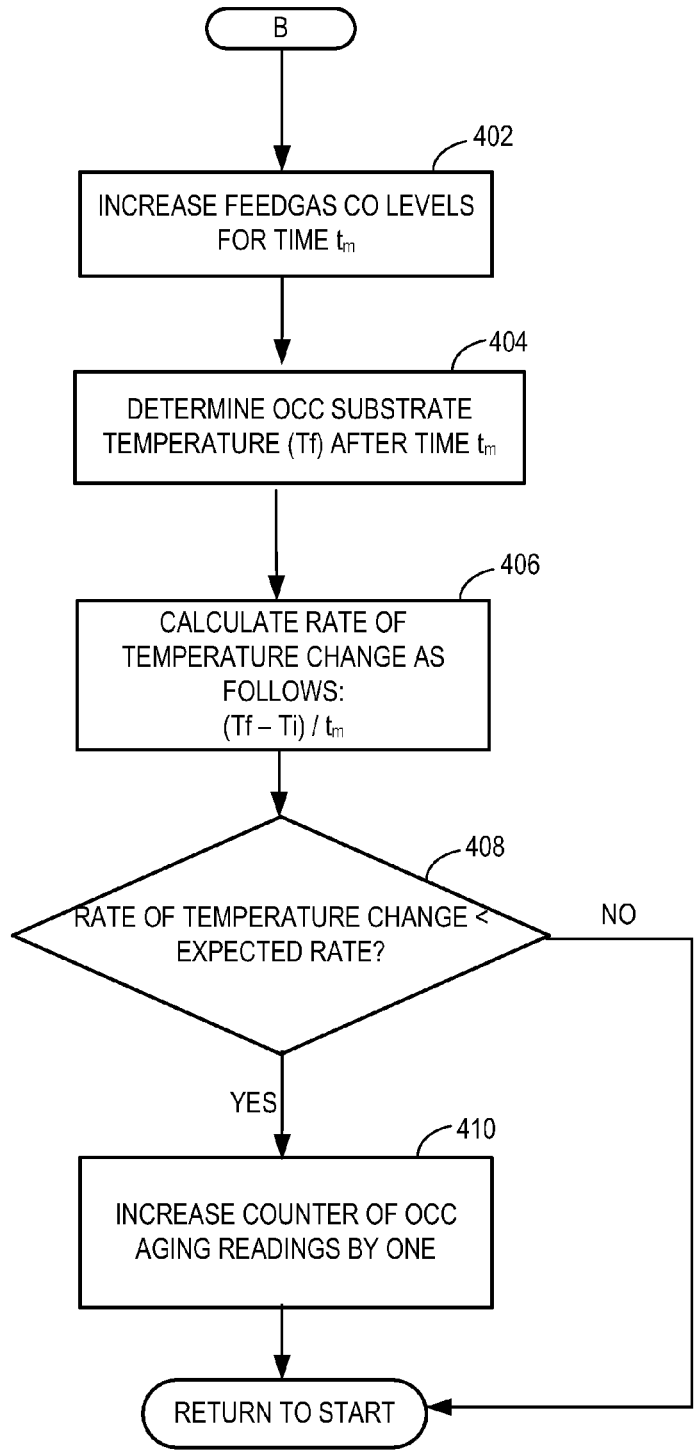
FIG. 4 portrays a flowchart demonstrating a routine for analyzing oxidation action of an OCC based on temperature rise within the catalytic converter.

Turning now to FIG. 3, it describes an example routine 300 that demonstrates type A of OCC aging diagnosis performed by the controller when an additional CO sensor is present downstream from the OCC. Specifically, routine 300 calculates a CO oxidation efficiency based on a difference in CO concentration readings pre- and post-OCC and compares the calculated oxidation efficiency with an expected efficiency. Multiple readings may be obtained to ensure higher reliability of the diagnosis.

At 302, a CO concentration in exhaust gases entering the OCC (CO_IN) may be determined from a sensor placed upstream of the OCC. In the embodiment of FIG. 1, sensor 126 may be a CO sensor placed in the exhaust manifold to measure CO_IN. At 304, CO concentration in gases exiting the OCC (CO_OUT) may be determined from a CO sensor placed downstream of the catalyst. In the engine depicted in FIG. 1, sensor 96 may measure CO_OUT.

At 306, a CO oxidation efficiency may be estimated based on the percentage relative change between CO_IN and CO_OUT. For example, when feedgas CO levels (CO_IN) entering the OCC are 3000 ppm and CO levels in gases exiting the OCC (CO_OUT) are 1200 ppm, oxidation efficiency can be calculated to be 60%.

Next at 308, the calculated oxidation efficiency may be compared with an expected oxidation efficiency at that temperature. If it is determined that the calculated efficiency is lower than expected efficiency, at 310, the controller increments a counter of OCC aging readings by one and returns to start. On the other hand, if calculated efficiency is determined to be comparable to an expected oxidation efficiency, the routine returns to start without incrementing the counter and waits to perform the diagnostic again when necessary conditions are met.

In this way, degradation of oxidation action within the OCC due to aging may be evaluated by using two sensors that measure CO levels pre- and post-OCC. By calculating CO oxidation efficiency under enhanced CO levels in the feedgas, more accurate data may be obtained. However, type A diagnostic requires at least two CO sensors and can increase costs associated with such a system.

Figure 9:
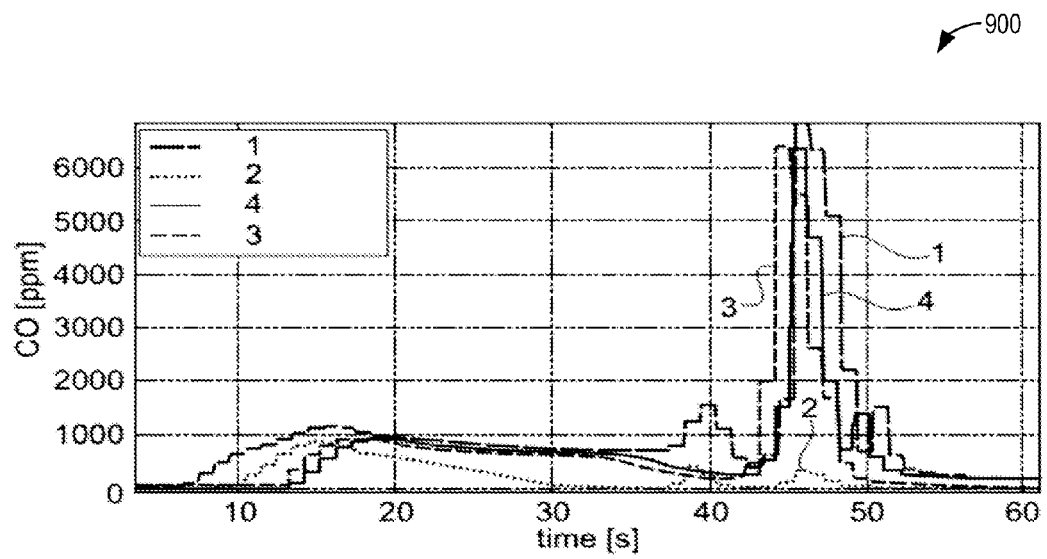
FIG. 9 shows the variation in carbon monoxide content of exhaust gas streams, plotted over time, according to the present disclosure.

FIG. 9 depicts a comparison in carbon monoxide leakage between an aged and a non-aged OCC in map 900. Curves 1 and 2 correspond to CO content upstream and downstream of a non-aged OCC respectively, while curves 3 and 4 show the corresponding CO content upstream and downstream of an aged oxidizing catalytic converter respectively. The diagnosis may commence once the OCC substrate temperature has reached 150° C. which is the light-off temperature. An artificial increase in CO levels in the exhaust gas stream may be generated for a period of about five-nine seconds after light-off. This artificial increase in CO levels is observed as a rapid rise in CO content in the exhaust gas stream from well below 2000 ppm to more than 5000 ppm between about 43 and 50 seconds on the X-axis. The oxidizing action of the non-aged oxidizing catalytic converter can be noted by comparing curves 1 and 2. Curve 1 representing feedgas CO concentration reaches about 6500 ppm at about 45 seconds while the CO content downstream of the OCC (curve 2) remains well below 1000 ppm and shows an insignificant rise to about 300 ppm at about 45 seconds. Thus, it can be inferred that the OCC oxidizes the CO within the exhaust gas stream very efficiently.

By contrast, a corresponding comparison for curves 3 and 4 shows that the aged OCC possesses a markedly lower oxidizing action and the CO content downstream of the OCC (curve 4) is barely lower than it is upstream level (curve 3). Feedgas CO levels and downstream CO levels are each at about 6000 ppm at 45 seconds indicating minimal oxidation within the OCC. Thus, the degree of aging of the OCC can be evaluated by measuring the CO content downstream of the OCC (also termed, carbon monoxide leakage) and a corresponding oxidation efficiency.

Referring now to FIG. 4, it shows an example routine 400 depicting type B of aging diagnosis that may be performed by the controller based on a measured temperature rise within the OCC during oxidation. Specifically, a rate of temperature rise is measured and correlated to an aged OCC if the temperature rise is slower than an expected rate of rise. Multiple readings may be obtained to ensure higher reliability.

At step 402, the time for which an artificial increase in CO is generated may be noted as $t_m$. As shown in FIG. 9, the CO levels may be increased from about 500 ppm to about 6000 ppm for a duration of about 5 seconds. Thus, $t_m$ may be noted as 5 seconds.

At 404, the OCC substrate temperature after time $t_m$ may be determined and noted as Tf. In one example, multiple measurements of the OCC substrate temperature may be obtained for specific intervals of time, for e.g., $t_m$, to improve reliability of the data. At 406, a rate of temperature change may be calculated as follows:

$$(Tf-Ti)/t_m$$

Where,
Tf=temperature of OCC substrate after time $t_m$
Ti=temperature of OCC substrate before CO levels are increased (step 210 in routine 200), and,
$t_m$=time interval during which CO levels are increased At 408, it may be confirmed if the rate of temperature change is lower than an expected rate. If it is confirmed that the rate of substrate temperature rise is slower than expected, at step 410, a counter of OCC aging readings may be increased by one. If the rate of temperature rise is equal to or more than an expected rise, the routine returns to start and continues to run the diagnostic sequence when operating conditions are met.

In this way, the exothermic oxidation reaction of carbon monoxide within the OCC may be utilized to diagnose the aging of an OCC. Type B diagnostic utilizes the fact that the temperature of an aged OCC rises more slowly than that of a fresh, robust OCC. Further, since an OCC may usually possess a temperature sensor to detect (and avoid) imminent overheating of the OCC, no additional hardware is required for this type of diagnosis. Thus, type B diagnosis can be carried out without any increase in overall costs.

Figure 10:
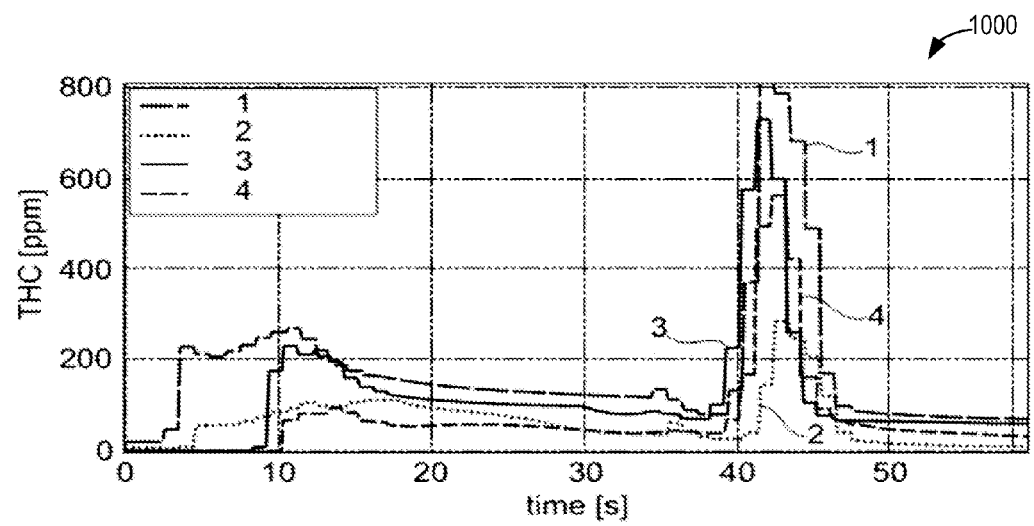
FIG. 10 shows the variation in hydrocarbons in the exhaust gas streams, plotted over time, according to the present disclosure.

FIG. 10 shows a map 1000 which portrays the variation in hydrocarbon (HC) content during the aging diagnosis plotted against time. Curves 1 and 2 correspond to HC content upstream and downstream of a non-aged OCC respectively, while curves 3 and 4 show the corresponding HC content upstream and downstream of an aged oxidizing catalytic converter respectively. When an exhaust gas stream containing increased levels of CO is generated, a rise in the overall content of hydrocarbons (THC, total hydrocarbons) also occurs. However, the absolute values with peaks of about 800 ppm remain very low, as compared with the CO contents illustrated in FIG. 9, and therefore, provide a significantly minor contribution to increasing the substrate temperature of the OCC. For example, in an exhaust gas stream with a CO content of 10000 ppm and an overall HC content of 1000 ppm, the CO may produce a temperature rise of about 100° C. while the HC content may cause a rise of about 20° C. Thus, the influence of CO in the feedgas is about five times as great as that of the HC content. Essentially, an OCC substrate temperature increase during an aging diagnosis is largely in response to the artificial increase in CO levels in the exhaust gas stream and depends minimally upon the HC content. Further, any effect on temperature rise due to the oxidation of HC accumulated within the OCC prior to light-off is marginal.

Since CO does not accumulate within the OCC prior to light-off, an aging diagnosis based on temperature rise can be attributed largely to the oxidation of CO in the feedgas. Moreover, the temperature rise caused by oxidation of CO is markedly greater than that caused by the oxidation of HCs contributing to a higher evidential force and accuracy of using temperature rise as an indicator of OCC aging.

Figure 11:
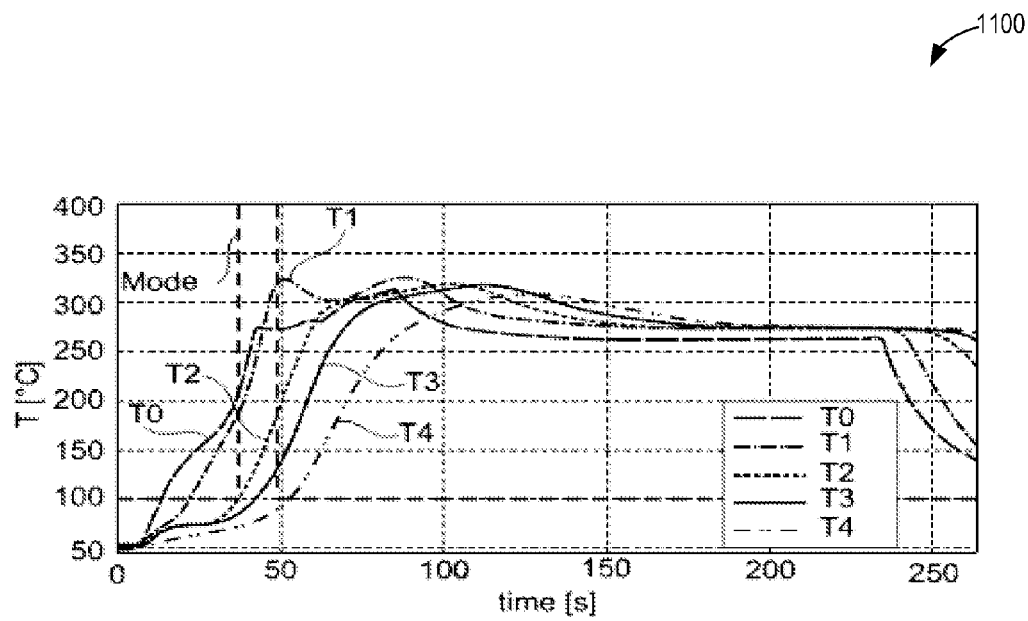
FIG. 11 shows temperature profiles for a non-aged or robust oxidizing catalytic converter, plotted over time, according to the present disclosure.

Turning now to FIG. 11 where map 1100 depicts temperature profiles for a non-aged OCC plotted over time. Herein, curve T0 shows the temperature upstream of the OCC. Curves T1 to T4 show temperature profiles for various locations within the OCC wherein temperature profile T1 may be measured at a point upstream to that of temperature profile T2 and so on. The local temperature distribution can be read off from the time delay between the various curve rises in the time range between 0 and 100 seconds, where curve T0 rises first and curve T4 rises last. Vertical lines "Mode" represent the interval when an artificial increase in CO levels is generated. This CO containing exhaust stream is induced upon OCC light-off or as soon as the temperature upstream of the OCC (curve T0) has reached 200° C.

From FIG. 11 it can be noted that as oxidation occurs within the OCC, temperatures for all locations within the OCC reach approximately the same values after a period of time, about 200 seconds. The temperature within the OCC is about 20° C. higher than the temperature upstream of the OCC (curve T0) because of the exothermic oxidation reaction occurring in the OCC.

Figure 12:
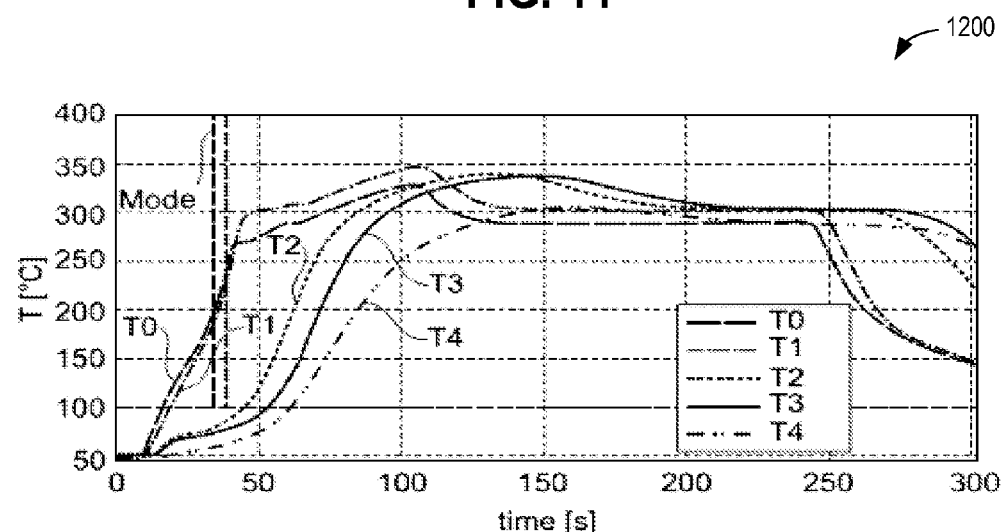
FIG. 12 shows temperature profiles for an aged oxidizing catalytic converter, plotted over time, according to the present disclosure

FIG. 12 shows map 1200 illustrating temperature profiles for an aged OCC plotted over time where the curves correspond to those in FIG. 11. Thus, curve T0 shows the temperature upstream of the OCC while curves T1 to T4 show temperature profiles for various locations within the OCC wherein temperature profile T1 may be measured at a point upstream to that of temperature profile T2 and so on. It may be noted that curves T1 to T4 show comparable temperature levels after about 200 seconds and therefore, a degree of aging of the OCC cannot be estimated solely from FIG. 12.

Figure 13:
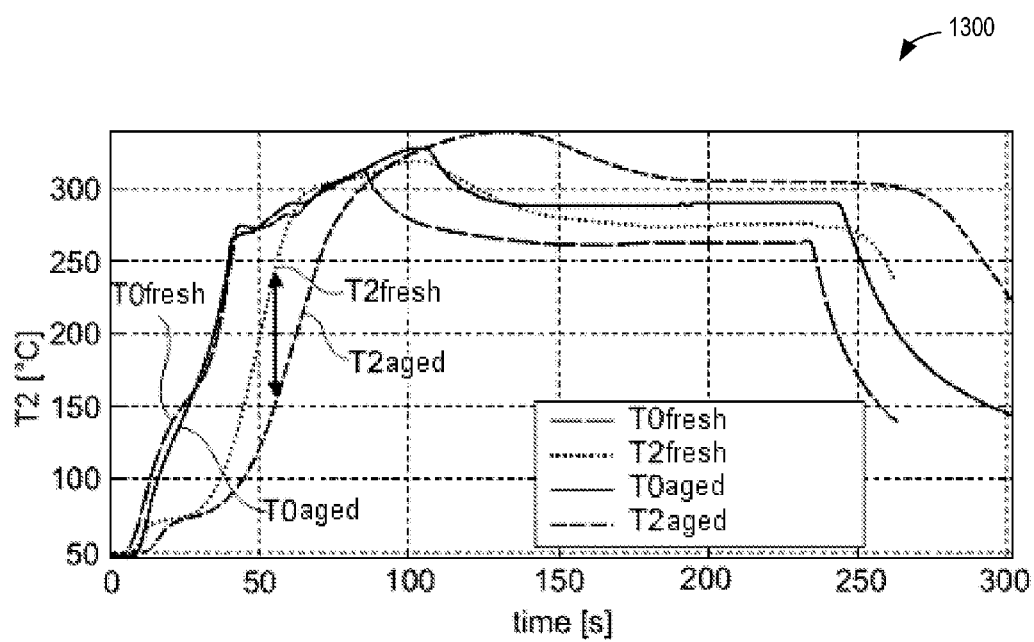
FIG. 13 shows a comparison of temperature profiles for an aged and a non-aged (robust) OCC, from FIGS. 11 and 12.

Turning now to FIG. 13 where map 1300 is a comparison of temperature profiles wherein curves T0 and T2 from FIGS. 11 and 12 are shown on the same map. It may be noted that temperature profiles T0 for the aged and non-aged OCC possess very similar curve shapes and that the temperatures upstream of the OCC are essentially identical. Any minor deviations may be attributed to ever-present fluctuations during successive tests. However, curves T2 for the aged and non-aged OCC show marked deviations from one another. The slope of curve T2 for the non-aged OCC is higher than that of the aged OCC through the time range of 40-75 seconds in plot 1300. Further, there is a significant gap between the two T2 curves since the aged OCC is at a lower temperature consistently through the same time range. The non-aged OCC oxidizes a larger quantity of CO and therefore, its temperature measured at the same location as that of the non-aged OCC is higher and rises faster. Correspondingly, temperature T2 for the aged OCC which oxidizes less CO, rises relatively slowly and with a marked delay. The degree of aging of the OCC can therefore be obtained by measuring the temperature rise within the OCC.

By performing a series of tests for a non-aged, robust OCC for a specific engine under various operating conditions, a set of data denoting an expected temperature rise at a specific location within the OCC may be determined. By comparing these expected values to temperature changes observed within an OCC as it ages, it is possible to determine the degree of aging of the OCC.

As shown in FIG. 13, in one example, oxidizing action can be determined by measuring the temperature within the OCC after a specific time span following the artificial increase in CO levels. If the OCC is more aged, the measured temperature is lower whereas in an OCC that is more robust, the measured temperature is higher. In another example, the rate of temperature increase can be measured to determine the degree of aging. In a less aged OCC, the rate of temperature increase will be higher than the rate of temperature increase within an aged catalyst.

An example OCC aging diagnosis illustrating the two diagnostic types is now described with reference to FIGS. 7 and 8. Map 700 of FIG. 7 depicts an example type A diagnosis wherein oxidation action is determined by measuring CO oxidation efficiency. As described earlier in reference to FIG. 3, type A diagnosis may be performed when the engine comprises two CO sensors in the exhaust system that can measure CO levels upstream and downstream of the OCC.

Map 700 depicts OCC diagnosis results at plot 702, air fuel (A/F) ratio at plot 704, expected CO oxidation efficiency at plot 706, calculated CO oxidation efficiency at 708, OCC substrate temperature at plot 710, and measured CO output from engine at plot 712. All plots are depicted over time, plotted along the x-axis. Additionally, line 707 represents a minimum threshold limit for CO oxidation efficiency which in one example could be 50% oxidation. Line 713 represents the minimum threshold limit, for e.g., the light-off temperature, for OCC substrate temperature and line 717 corresponds to a minimum threshold of CO levels in exhaust gases. The vehicle comprising the OCC in its exhaust treatment system may be operated from time t1 to t5 and then again from t6 to past t10 (not shown on map 700).

Prior to t1, carbon monoxide (CO) levels are below the threshold according to emission requirements. As the engine continues to operate, OCC temperature rises and at t1 reaches light-off temperature which as explained earlier in reference to FIG. 5 may be 150° C. The oxidation efficiency of the OCC may be about 50% at t1. At t1, therefore, an aging diagnosis may commence by artificially increasing CO levels in the exhaust stream for a short duration via operating the engine in a lean mode possibly under cold engine conditions. Between t1 and t2, the CO content increases and the oxidation efficiency may be calculated and found to be comparable to an expected efficiency (plots 706 and 708 between t1 and t2). At t2, at the end of the diagnosis, CO levels are reduced to decrease any negative impact on emissions. However, CO levels in feedgas remain above the minimum threshold 717 between t2 and t3. Another series of testing may be performed since OCC temperature is above light-off and the oxidation efficiency may be in the peak range. Thus, CO levels are increased again but to a lesser extent since the CO levels in the exhaust stream are higher than those prior to t1 (as elaborated earlier with reference to FIG. 6). Between t3 and t4, the oxidation efficiency may be calculated again and found to be comparable to an expected efficiency (plots 706 and 708 between t3 and t4). Thus, the OCC may be diagnosed as being robust and non-aged (plot 702). At t4, the second series of tests may be concluded and CO levels may be decreased to below the threshold and at t5 the vehicle may be stopped.

Between t5 and t6, an extended time interval is indicated during which the vehicle may be used consistently. Note that the plots after t6 are an example of a diagnosis for an aged OCC.

At t6, the vehicle may begin operating and the OCC temperature rises slowly and at t7 reaches the light-off temperature. Between t7 and t10 the same diagnoses steps may be performed as described above between t1 and t5. However, the calculated oxidation efficiency (plot 708) is observed to be significantly lower than expected efficiency (plot 706) during the diagnoses performed between t7-t8 and t9-t10. Therefore, based on these results, the controller indicates an aged OCC as shown in plot 702 between t7 and t10.

Turning now to FIG. 8 comprising map 800 depicting an example type B diagnosis for detecting aging using temperature rise within the OCC during oxidation. Type B diagnosis uses a temperature sensor placed in the OCC and does not require an additional CO sensor.

Map 800 depicts OCC diagnosis results at plot 802, air fuel (A/F) ratio at plot 804, expected oxidation action as a function of rate of temperature change at plot 806, calculated oxidation action as a function of rate of temperature change at 808, OCC substrate temperature at plot 810, and measured CO output from engine at plot 812. All plots are depicted over time, plotted along the x-axis. Additionally, line 813 represents the minimum threshold limit for OCC substrate temperature and line 817 corresponds to a minimum threshold of CO levels in exhaust gases. The vehicle comprising the OCC in its exhaust treatment system may be operated from time t1 to t5 and then again from t6 to past t10 (not shown on map 800).

Prior to t1, carbon monoxide (CO) levels are below the threshold according to emission requirements. As the engine continues to operate, OCC temperature rises and at t1 reaches light-off temperature which as explained earlier in reference to FIG. 5 may be 150° C. At t1, therefore, an aging diagnosis may commence by artificially increasing CO levels in the exhaust stream for a short duration via operating the engine in a lean mode possibly under cold engine conditions. Between t1 and t2, the CO content increases and the speed of temperature rise may be calculated and found to be comparable to an expected rate of temperature rise (plots 806 and 808 between t1 and t2). Multiple readings may be obtained within this time interval. At t2, the CO levels are reduced to decrease any negative impact on emissions. However, CO levels in feedgas remain above the minimum threshold 817 between t2 and t3. Another series of testing may be performed since OCC temperature is above light-off between t3 and t4. Thus, CO levels are increased again but to a lesser extent since the CO levels in the exhaust stream are higher than those prior to t1 (as elaborated earlier with reference to FIG. 6). Between t3 and t4, the oxidation action may be calculated again and found to be comparable to an expected efficiency (plots 806 and 808 between t3 and t4). Thus, the OCC may be diagnosed as being robust and non-aged (plot 802). At t4, the second series of tests may be concluded and CO levels may be decreased to below the threshold and at t5 the vehicle may be stopped.

Between t5 and t6, an extended time interval is indicated during which the vehicle may be used consistently. As such the plots after t6 are an example of a diagnosis of an aged OCC.

At t6, the vehicle may begin operating and the OCC temperature rises slowly to reach the light-off temperature at t7. Between t7 and t10 the same diagnoses steps may be performed as described above between t1 and t5. It may be noted that the substrate temperature rises at a slower rate between t7-t8 and t9-t10 as compared with the temperature rise between t1-t2 and t3-t4. The calculated rate of temperature change (plot 808) is observed to be significantly lower than expected rate of temperature change (plot 806) during the diagnoses performed between t7-t8 and t9-t10. Therefore, based on these oxidation action results, the controller indicates an aged OCC as shown in plot 802 between t7 and t10.

It will be appreciated that though not described above, an additional type of diagnostic for determining the aging of an OCC may be based exclusively on the temperature rise within the OCC. For example, the temperature at a precise location in a non-aged OCC may be measured at specific times after the CO levels in the exhaust stream are increased. These readings may be stored in the controller memory. To determine an aged catalyst, the temperature within the OCC may again be measured at the same time(s) past the onset of an increased CO exhaust stream. A lower temperature within the OCC compared with that of a non-aged OCC may be indicative of aging. In one example, the temperature may be measured by a sensor located within a brand new, non-aged OCC 50 seconds after increased levels of CO are generated. This reading may be stored in the controller memory. Aging of the same OCC may be evaluated after about 5 years by measuring the temperature at the same location within the OCC and at 50 seconds after the onset of a CO laden exhaust stream. If the temperature of the OCC in the latter measurement is lower than that of a non-aged OCC, aging is indicated.

In this way, an oxidizing catalytic converter (OCC) may be diagnosed for a degree of aging by temporarily augmenting carbon monoxide (CO) levels in the exhaust stream and using either a measure of oxidation efficiency or temperature rise within the OCC to detect degradation due to aging. Higher temperatures may be generated within the OCC as CO oxidation occurs which enhances the reliability of temperature data unlike tests performed based on augmented hydrocarbon levels which produce smaller temperature changes. By relying on increased levels of CO in the exhaust stream instead of increased hydrocarbons (HC), errors in temperature readings due to the oxidation of hydrocarbons accumulated within the OCC when below light-off temperature are reduced. This is because CO does not accumulate within the OCC prior to light-off. Further, since CO levels are increased only after the OCC has reached light-off temperature, emissions may be maintained below threshold levels. Thus, OCC aging may be assessed with minimal negative effects on emissions.

Note that the example control and estimation routines included herein can be used with various engine and/or vehicle system configurations. The control methods and routines disclosed herein may be stored as executable instructions in non-transitory memory. The specific routines described herein may represent one or more of any number of processing strategies such as event-driven, interruptdriven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for determining a degree of aging of an oxidizing catalytic converter arranged in an exhaust of a compression ignition diesel internal combustion engine comprising:
   operating the compression ignition internal combustion engine in a lean mode to combust air and diesel fuel through compression ignition to temporarily increase carbon monoxide levels in the exhaust upstream of the oxidizing catalytic converter and maintain a larger proportion of carbon monoxide than hydrocarbons in the exhaust, where operating the compression ignition internal combustion engine in the lean mode includes manipulating an air-fuel ratio from a lean air-fuel ratio, prior to operating in the lean mode, to a leaner air-fuel ratio, during operating in the lean mode;
   measuring an oxidizing action of the oxidizing catalytic converter in response to the increased carbon monoxide levels; and
   determining a degree of aging of the oxidizing catalytic converter as a function of the measured oxidizing action of the oxidizing catalytic converter.

2. The method of claim 1, wherein during increasing the carbon monoxide levels, the exhaust contains more carbon monoxide than C1 hydrocarbons and wherein operating the internal combustion engine in the lean mode includes increasing the air-fuel ratio of the internal combustion engine to increase the carbon monoxide levels in the exhaust by an amount of increase in carbon monoxide, wherein the amount of increase in carbon monoxide decreases as carbon monoxide levels in the exhaust, prior to the temporarily increasing, increases.

3. The method of claim 1, wherein during increasing the carbon monoxide levels, the exhaust contains at least 2500 ppm of carbon monoxide.

4. The method of claim 1, wherein during increasing the carbon monoxide levels, the exhaust contains less than 1500 ppm of C1 hydrocarbons.

5. The method of claim 1, wherein the oxidizing action of the oxidizing catalytic converter is evaluated by measuring a carbon monoxide leakage of the oxidizing catalytic converter.

6. The method of claim 1, wherein, before operating the internal combustion engine in the lean mode to temporarily increase carbon monoxide levels in the exhaust, a substrate temperature of the oxidizing catalytic converter is determined and the operating the internal combustion engine in the lean mode to temporarily increase carbon monoxide levels in the exhaust only occurs when the substrate temperature lies above a light-off temperature of the oxidizing catalytic converter^ and further comprising turning on a malfunction indicator lamp on a dashboard in response to the determined degree of aging being higher than a threshold.

7. The method of claim 1, further comprising evaluating the oxidizing action of the oxidizing catalytic converter by measuring a temperature of the oxidizing catalytic converter.

8. The method of claim 7, wherein the oxidizing action of the oxidizing catalytic converter is evaluated by measuring a rise in the temperature of the oxidizing catalytic converter.

9. The method of claim 8, wherein the oxidizing action of the oxidizing catalytic converter is evaluated by determining a speed of the temperature rise.

10. The method of claim 9, wherein a higher degree of aging is established in the case of a lower speed of temperature rise and a lower degree of aging is established in the case of a higher speed of temperature rise.

11. A method for monitoring performance of an oxidizing catalytic converter in a compression ignition diesel engine comprising:
   manipulating an air-fuel ratio of the compression ignition diesel engine to operate the engine in a lean mode to increase carbon monoxide levels in an exhaust stream output from the engine, where the exhaust stream includes a larger proportion of carbon monoxide than hydrocarbons during the operating in the lean mode, where manipulating the air-fuel ratio of the engine to operate the engine in the lean mode to increase carbon monoxide levels in the exhaust stream output from the engine includes increasing the air-fuel ratio from a lean air-fuel ratio, prior to the manipulating the air-fuel ratio to operate the engine in the lean mode, to a leaner air-fuel ratio and maintaining the leaner air-fuel ratio until an end of a diagnosis of the oxidizing catalytic converter;
   monitoring oxidizing action of the oxidizing catalytic converter during the manipulating the air-fuel ratio; and
   indicating aging based on the monitored oxidizing action.

12. The method of claim 11, wherein the oxidizing action is monitored by measuring carbon monoxide oxidation efficiency of the oxidizing catalytic converter.

13. The method of claim 11, wherein the air-fuel ratio is manipulated to operate the engine in the lean mode to increase carbon monoxide levels in the exhaust stream only when the oxidizing catalytic converter is above a light-off temperature and wherein indicating aging based on the monitored oxidizing action includes one or more of displaying a message to a vehicle operator that degradation has been identified and setting a diagnostic code stored in non-transitory memory of a controller of the engine corresponding to aging of the oxidizing catalytic converter.

14. The method of claim 11, wherein the exhaust stream contains more carbon monoxide than C1 hydrocarbons and.

15. The method of claim 11, wherein the oxidizing action is monitored by measuring a temperature rise in the oxidizing catalytic converter.

16. The method of claim 15, wherein aging of the oxidizing catalytic converter is indicated responsive to a lower speed of temperature rise.

17. A system for a compression ignition diesel engine in a vehicle comprising:
- an oxidizing catalytic converter;
- one or more carbon monoxide or oxygen sensors;
- one or more temperature sensors; and
- a controller with computer readable instructions stored in non-transitory memory for:
  - when an oxidizing catalytic converter temperature is above light-off,
    - artificially increasing carbon monoxide levels in exhaust output by the engine and adjusting the exhaust to contain more carbon monoxide than C1 hydrocarbons by operating the engine in a lean mode, where operating the engine in the lean mode includes manipulating an air-fuel ratio of the engine from a lean, first air-fuel ratio to a leaner, second air-fuel ratio;
  - evaluating oxidation action of the oxidizing catalytic converter during the artificial increase in carbon monoxide levels; and
  - indicating aging of the oxidizing catalytic converter based on the evaluated oxidation action.

18. The system of claim 17, wherein the oxidation action is evaluated by measuring carbon monoxide oxidation efficiency, and further comprising, after evaluating the oxidation action of the oxidizing catalytic converter, returning the air-fuel ratio of the engine to the lean, first air-fuel ratio.

19. The system of claim 17, wherein the oxidation action is evaluated by monitoring temperature rise within the oxidizing catalytic converter and aging is indicated based on a slower temperature rise, where an amount of artificial CO increase is based on an amount of CO in the exhaust.

* * * * *